United States Patent
Sarac et al.

(10) Patent No.: US 8,182,522 B2
(45) Date of Patent: May 22, 2012

(54) APPARATUS AND METHOD FOR DELIVERING LINED INTRALUMINAL PROSTHESES

(75) Inventors: Timur P. Sarac, Chagrin Falls, OH (US); Rajesh Khosla, Beachwood, OH (US); David Halpern, Beachwood, OH (US); James Edward Barber, Avon, OH (US)

(73) Assignees: The Cleveland Clinic Foundation, Cleveland, OH (US); Peritec Biosciences, Ltd., Cleveland, OH (US)

( * ) Notice: Subject to any disclaimer, the term of this patent is extended or adjusted under 35 U.S.C. 154(b) by 892 days.

(21) Appl. No.: 11/601,075

(22) Filed: Nov. 16, 2006
(Under 37 CFR 1.47)

(65) Prior Publication Data

US 2007/0265694 A1    Nov. 15, 2007

Related U.S. Application Data

(60) Provisional application No. 60/738,107, filed on Nov. 17, 2005.

(51) Int. Cl.
*A61F 2/06* (2006.01)

(52) U.S. Cl. ..................................................... 623/1.11

(58) Field of Classification Search ............... 604/63.01, 604/96.01, 264; 606/108, 191, 194, 200; 623/1.11–1.13, 1.23
See application file for complete search history.

(56) References Cited

U.S. PATENT DOCUMENTS

| 4,553,545 | A |   | 11/1985 | Maass et al. |
| 4,665,918 | A | * | 5/1987 | Garza et al. .................. 606/108 |
| 4,776,337 | A |   | 10/1988 | Palmaz |
| 5,376,110 | A |   | 12/1994 | Tu et al. |
| 5,534,007 | A |   | 7/1996 | St. Germain et al. |
| 5,571,166 | A |   | 11/1996 | Dinh et al. |
| 5,626,603 | A | * | 5/1997 | Venturelli et al. ........... 623/1.11 |
| 5,746,764 | A |   | 5/1998 | Green et al. |
| 5,746,766 | A |   | 5/1998 | Edoga |
| 5,810,838 | A |   | 9/1998 | Solar |

(Continued)

FOREIGN PATENT DOCUMENTS

EP    0 948 946 A1    10/1999

(Continued)

OTHER PUBLICATIONS

Copending U.S. Sarac et al. Patent Application filed Nov. 16, 2006 entitled Method and Apparatus for Compressing Intraluminal Prostheses'.

*Primary Examiner* — Ryan Severson
*Assistant Examiner* — Ashley Cronin
(74) *Attorney, Agent, or Firm* — Tarolli, Sundheim, Covell & Tummino LLP

(57) ABSTRACT

An apparatus for delivering an intraluminal prosthesis within a patient's body includes an inner sheath having longitudinally spaced proximal and distal inner sheath ends, and a nose cone connected to the distal inner sheath end. An intraluminal prosthesis sheath has longitudinally spaced proximal and distal intraluminal prosthesis sheath ends and a hollow intraluminal prosthesis sheath bore at least partially surrounding the inner sheath. A stopper is connected to the inner sheath at a location longitudinally spaced from the nose cone and extends radially between the inner sheath and the intraluminal prosthesis sheath. An annular intraluminal prosthesis space is defined radially between the intraluminal prosthesis sheath and the inner sheath and longitudinally between the stopper and the nose cone. A method for delivering an intraluminal prosthesis within a patient's body is also described.

20 Claims, 4 Drawing Sheets

U.S. PATENT DOCUMENTS

| | | |
|---|---|---|
| 5,860,966 A | 1/1999 | Tower |
| 5,911,752 A | 6/1999 | Dustrude et al. |
| 5,922,393 A | 7/1999 | Jayaraman |
| 5,944,735 A | 8/1999 | Green et al. |
| 5,971,992 A | 10/1999 | Solar |
| 5,972,028 A | 10/1999 | Rabenau et al. |
| 6,009,614 A | 1/2000 | Morales |
| 6,045,568 A | 4/2000 | Igaki et al. |
| 6,063,092 A | 5/2000 | Shin |
| 6,183,503 B1 | 2/2001 | Hart et al. |
| 6,249,952 B1 | 6/2001 | Ding |
| 6,295,714 B1 | 10/2001 | Roychowdhury et al. |
| 6,352,547 B1 | 3/2002 | Brown et al. |
| 6,387,117 B1 | 5/2002 | Arnold, Jr. et al. |
| 6,416,544 B2 | 7/2002 | Sugita et al. |
| 6,582,472 B2 | 6/2003 | Hart |
| 6,685,735 B1 | 2/2004 | Ahari |
| 6,745,445 B2 | 6/2004 | Spilka |
| 6,755,855 B2 | 6/2004 | Yurek et al. |
| 6,790,221 B2 | 9/2004 | Monroe et al. |
| 6,821,291 B2 | 11/2004 | Bolea et al. |
| 6,860,898 B2 | 3/2005 | Stack et al. |
| 6,878,158 B2 | 4/2005 | Shin et al. |
| 6,915,560 B2 | 7/2005 | Austin |
| 2004/0181236 A1 | 9/2004 | Eidenschink et al. |
| 2005/0033404 A1 | 2/2005 | Eidenschink |
| 2005/0165352 A1 | 7/2005 | Henry et al. |
| 2005/0267562 A1 | 12/2005 | Jones et al. |

FOREIGN PATENT DOCUMENTS

| | | |
|---|---|---|
| EP | 0 970 711 A2 | 1/2000 |
| EP | 0 970 711 A3 | 1/2001 |
| EP | 1 095 634 A2 | 5/2001 |
| EP | 1 226 798 A2 | 7/2001 |
| EP | 0 970 711 B1 | 10/2004 |
| WO | WO 96/00099 | 1/1996 |
| WO | WO 99/33410 A2 | 7/1999 |
| WO | WO 99/33410 A3 | 7/1999 |

* cited by examiner

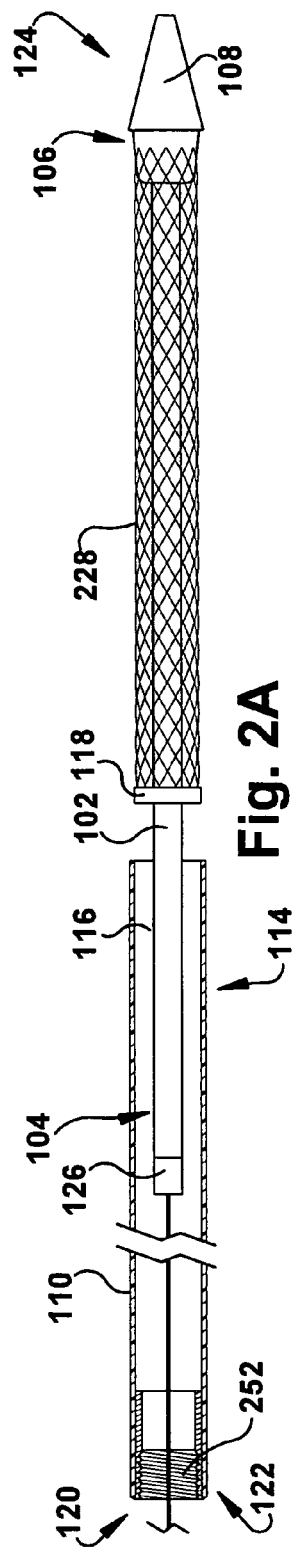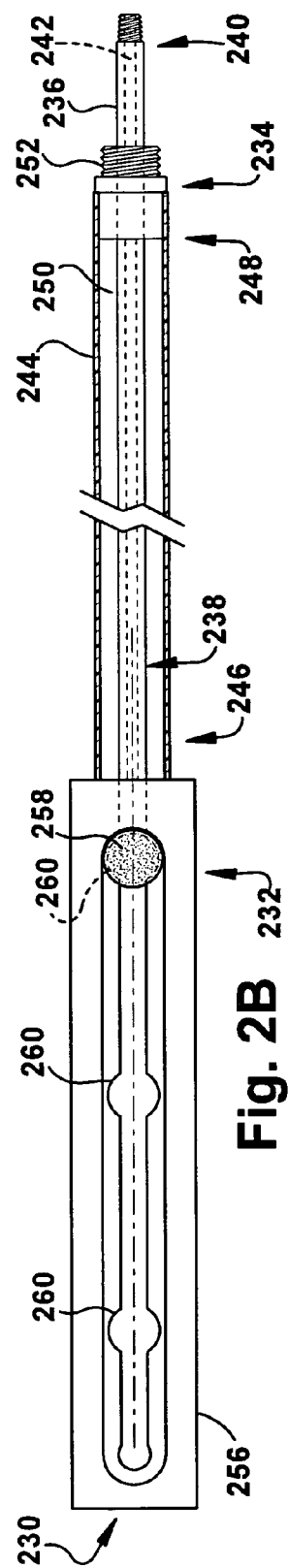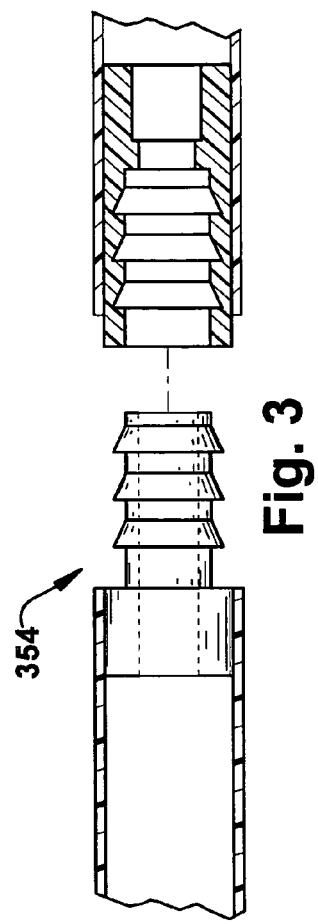

Table of Contents
APPARATUS AND METHOD FOR DELIVERING LINED INTRALUMINAL PROSTHESES

RELATED PATENT APPLICATION

This application claims priority from U.S. Provisional Patent application Ser. No. 60/738,107, filed Nov. 17, 2005, the subject matter of which is incorporated herein by reference.

TECHNICAL FIELD

The present invention relates to an apparatus and method for use of a lined intraluminal prosthesis and, more particularly, to an apparatus and method for delivering a compressed lined intraluminal prosthesis to a desired location within a patient's body.

BACKGROUND OF THE INVENTION

Heart attacks are a leading cause of death in the industrialized world. Many heart attacks are caused in part by narrowed, stenosed coronary blood vessels. One medical procedure commonly used to deal with coronary vessel stenosis is angioplasty. Angioplasty, in particular Percutaneous Transluminal Coronary Angioplasty (PTCA), involves inserting a balloon catheter into the femoral artery near the groin, and advancing the catheter over the aortic arch and into a coronary artery. The balloon can be advanced through the coronary artery to the stenosis and inflated to widen or dilate the narrowed region. The balloon catheter can then be withdrawn. In some cases, the widened coronary vessel rebounds or re-closes, narrowing the vessel again over a period of time.

Intraluminal prostheses, such as a stent, graft, patch, or the like, are increasingly used to prevent the widened vessel regions from narrowing again after angioplasty. An intraluminal prosthesis, typically having a tubular shape, can be put in place in the widened vessel region to hold the vessel walls apart and the lumen of the vessel open in the event the vessel attempts to narrow again. One class of intraluminal prostheses requires that the intraluminal prosthesis be forcibly outwardly expanded, such as with a balloon catheter, to place the intraluminal prosthesis into position against the vessel walls. Another class of intraluminal prostheses, self-expanding intraluminal prostheses, can be delivered to a site in a compressed or constrained configuration and released in the vessel region to be supported. The self-expanding intraluminal prosthesis then expands in place to a configuration having a wide lumen, typically pressing firmly against the vessel walls where released. Self-expanding intraluminal prostheses are often elastically biased to assume an original larger shape after being temporarily compressed into a smaller size to more easily be transported through blood vessels to the target site. The intraluminal prosthesis is commonly placed at a recently dilated, stenosed vessel region.

Self-expanding intraluminal prostheses can be delivered to a target site via catheter, mounted over an inner tube or shaft and constrained within the distal end of an enclosing retractable tube or sleeve. The self-expanding intraluminal prosthesis can be freed from the restraint of the outer sheath by either distally pushing the inner shaft against the intraluminal prosthesis or proximally pulling the retractable outer sheath from over the intraluminal prosthesis. The release of the self-expanding intraluminal prosthesis must be done carefully to avoid tearing the intraluminal prosthesis or dragging the intraluminal prosthesis out of the desired position by the movement of the outer sheath. Once free of the restraint of the outer sheath, the self-expanding intraluminal prosthesis can expand to force itself against the vessel inner walls.

In general, a catheter should have a maximum radial extent or profile no larger than necessary, in part to enable the catheter to reach further into narrower vessel regions. The desired size of the intraluminal prosthesis to be delivered may not be known until the patient is in the operating or treatment room of a hospital. Therefore, many surgeons must choose an appropriately-sized intraluminal prosthesis and load it onto the catheter by hand while the patient is anesthesized. A self-expanding intraluminal prosthesis is most easily loaded in a proximal direction onto a catheter by compressing the intraluminal prosthesis and sliding the intraluminal prosthesis co-axially over the inner shaft distal end and within the retractable outer sheath. The intraluminal prosthesis must thus typically be slid over the catheter distal tip. The distal tip is optimally tapered into a nose cone having a proximal width about the same as the width of the outer sheath, to provide a smooth transition from the distal tip to the outer sheath. This can present a situation where the compressed intraluminal prosthesis has an inner diameter too small to be advanced over the larger outer diameter nose cone of the catheter. Even if the size of the compressed intraluminal prosthesis is chosen for loading over the nose cone, this process is very inefficient and may result in damage to the intraluminal prosthesis or adverse effects to the patient due to the increased time needed for the operation.

Moreover, intraluminal prostheses with a material lining the inside, outside, or both may present even more challenges for loading and delivery, particularly if the material is biological and its viability must be preserved.

It is known to crimp the intraluminal prosthesis onto the delivery catheter just prior to the implantation procedure. This was carried out manually in the operating room and could result in asymmetrical, uneven, or incomplete crimping. It was recognized that hand-crimping resulted in a non-optimal catheter/intraluminal prosthesis assembly and commercial suppliers began to provide pre-crimped intraluminal prosthesis/catheter kits. At the present, such prepared assemblies are in standard use for many types of intraluminal prosthesis delivery procedures. However, there are myriad combinations of intraluminal prosthesis diameter, intraluminal prosthesis length, intraluminal prosthesis material, intraluminal prosthesis configuration, catheter diameter, catheter length, and other variables which might be desired for many various procedures. It can be expensive and wasteful of time and space for a hospital to stock the wide selection of intraluminal prosthesis/catheter kits which might be needed across the spectrum of surgical intraluminal prosthesis procedures and patient types/sizes. Even if the necessary catheter size and intraluminal prosthesis type can be estimated before the procedure to narrow down the universe of possible intraluminal prosthesis/catheter kits which might be needed, the intraluminal prosthesis size may need to be determined during the procedure. A variety of intraluminal prosthesis/catheter kits, therefore, still must be made available in the operating room.

Accordingly, it is desirable to provide a method and apparatus of an intraluminal prosthesis delivery apparatus which avoids damage to the intraluminal prosthesis, allows surgeons to select an intraluminal prosthesis without regard to compressed size, and provides a modular system for efficiency and economy in storage and selection.

SUMMARY OF THE INVENTION

In an embodiment of the present invention, an apparatus for delivering an intraluminal prosthesis within a patient's body is described. An inner sheath has longitudinally spaced proximal and distal inner sheath ends. A nose cone is connected to the distal inner sheath end. An intraluminal prosthesis sheath has longitudinally spaced proximal and distal intraluminal prosthesis sheath ends and a hollow intraluminal prosthesis sheath bore at least partially surrounding the inner sheath. The intraluminal prosthesis sheath is adapted for movement relative to the inner sheath. A stopper is connected to the inner sheath at a location longitudinally spaced from the nose cone. The stopper extends radially between the inner sheath and the intraluminal prosthesis sheath. An annular intraluminal prosthesis space is defined radially between the intraluminal prosthesis sheath and the inner sheath and longitudinally between the stopper and the nose cone. The annular intraluminal prosthesis space is adapted to contain a compressed intraluminal prosthesis. The inner sheath, the nose cone, the stopper, the intraluminal prosthesis sheath, and the annular intraluminal prosthesis space cooperatively form an intraluminal prosthesis cartridge adapted for selective operative connection to a delivery catheter.

In an embodiment of the present invention, an intraluminal prosthesis delivery apparatus is described. An intraluminal prosthesis cartridge has longitudinally spaced proximal and distal cartridge ends and is adapted to contain a compressed intraluminal prosthesis. A delivery catheter has longitudinally spaced proximal and distal catheter ends and is adapted to guide the intraluminal prosthesis cartridge inside the patient's body. The distal catheter end and proximal cartridge end are selectively engageable to one another to form the apparatus.

In an embodiment of the present invention, a method for delivering an intraluminal prosthesis within a patient's body is described. An intraluminal prosthesis cartridge including an intraluminal prosthesis sheath is provided. A compressed intraluminal prosthesis is contained within the intraluminal prosthesis cartridge. The compressed intraluminal prosthesis is located radially within the intraluminal prosthesis sheath. A delivery catheter adapted to selectively control movement of the intraluminal prosthesis sheath is provided. The intraluminal prosthesis cartridge is guided with the delivery catheter to a desired intraluminal prosthesis placement location within the patient's body. The compressed intraluminal prosthesis from the intraluminal prosthesis cartridge is released at the desired intraluminal prosthesis placement location. The delivery catheter is manipulated to remove the intraluminal prosthesis cartridge from the patient's body while the intraluminal prosthesis remains at the desired placement location.

In an embodiment of the present invention, a method for delivering an intraluminal prosthesis within a patient's body is described. An intraluminal prosthesis cartridge including a cartridge inner sheath having longitudinally spaced proximal and distal cartridge inner sheath ends is provided. An intraluminal prosthesis sheath having longitudinally spaced proximal and distal intraluminal prosthesis sheath ends and a hollow intraluminal prosthesis sheath bore at least partially surrounding the cartridge inner sheath is also provided. A compressed intraluminal prosthesis is contained with the intraluminal prosthesis cartridge. The compressed intraluminal prosthesis is located radially between the intraluminal prosthesis sheath and the cartridge inner sheath. A delivery catheter including a catheter inner sheath having longitudinally spaced proximal and distal catheter inner sheath ends and a hollow catheter inner sheath bore is provided. The delivery catheter includes an outer sheath having longitudinally spaced proximal and distal outer sheath ends and a hollow outer sheath bore at least partially surrounding the catheter inner sheath. The delivery catheter also includes a handle attached to the proximal outer sheath end and the proximal catheter inner sheath end. The handle is adapted to selectively control longitudinal movement of the intraluminal prosthesis sheath. An inner sheath structure is formed with the cartridge inner sheath and the catheter inner sheath. An outer-intraluminal prosthesis sheath structure is formed with the intraluminal prosthesis sheath and the outer sheath. The inner sheath structure is contained within the outer-intraluminal prosthesis sheath structure. The intraluminal prosthesis cartridge, with the contained compressed intraluminal prosthesis, is inserted into the patient's body. The intraluminal prosthesis cartridge with the delivery catheter is guided to a desired intraluminal prosthesis placement location within the patient's body. The cartridge inner sheath and compressed intraluminal prosthesis are maintained at the desired placement location. The handle is actuated to move the intraluminal prosthesis sheath longitudinally away from the desired placement location. The compressed intraluminal prosthesis is released from the cartridge inner sheath as the intraluminal prosthesis sheath is moved. The compressed intraluminal prosthesis is expanded into the desired placement location to form an expanded intraluminal prosthesis. The delivery catheter is manipulated to remove the intraluminal prosthesis cartridge from the patient's body while the expanded intraluminal prosthesis remains at the desired placement location.

BRIEF DESCRIPTION OF THE DRAWINGS

For a better understanding of the invention, reference may be made to the accompanying drawings, in which:

FIG. 2A is a partial exploded side view of the embodiment of FIG. 1;

FIG. 2B is a partial exploded side view of the embodiment of FIG. 1;

FIG. 3 is a partial side view of the embodiment of FIG. 1;

DESCRIPTION OF EMBODIMENTS

Figure 1:
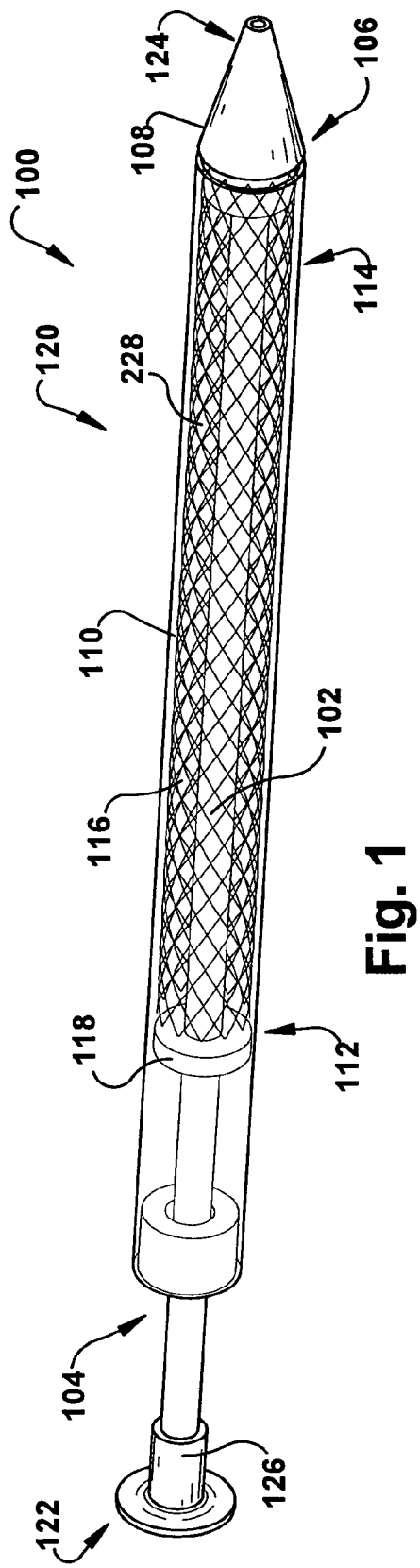
FIG. 1 is a partial perspective view of one embodiment of the present invention.

In accordance with the present invention, FIG. 1 depicts a portion of an apparatus 100 for delivering an intraluminal prosthesis 228 within a patient's body. The apparatus 100 includes a cartridge inner sheath 102 having longitudinally spaced proximal and distal cartridge inner sheath ends 104 and 106, respectively.

A nose cone 108 is connected to the distal cartridge inner sheath end 106. The nose cone 108 may have a reverse taper (not shown) on the front or back for ease in engaging with other structures as desired.

An intraluminal prosthesis sheath 110 has longitudinally spaced proximal and distal intraluminal prosthesis sheath ends 112 and 114, respectively, and a hollow intraluminal prosthesis sheath bore 116 which at least partially surrounds the cartridge inner sheath 102. The intraluminal prosthesis sheath 110 is adapted for longitudinal movement relative to the cartridge inner sheath 102 between a first, closed, position and a second, open, position.

A stopper 118 is connected to the cartridge inner sheath 102 at a location longitudinally spaced from the nose cone 108. The stopper 118 extends radially a substantial portion of the distance between the cartridge inner sheath 102 and the intraluminal prosthesis sheath 110, but need not entirely fill that distance.

An annular intraluminal prosthesis space is defined radially between the intraluminal prosthesis sheath 110 and the cartridge inner sheath 102 and longitudinally between the stopper 118 and the nose cone 108. The annular intraluminal prosthesis space is adapted to contain a compressed intraluminal prosthesis 228.

The cartridge inner sheath 102, nose cone 108, stopper 118, intraluminal prosthesis sheath 110, and annular intraluminal prosthesis space cooperatively form an intraluminal prosthesis cartridge 120 having longitudinally spaced proximal and distal cartridge ends 122 and 124 and adapted for selective operative connection to a delivery catheter (omitted from FIG. 1 for clarity). To help accomplish such, an inner sheath connector 126 may be provided on the proximal cartridge inner sheath end 104 to connect the cartridge inner sheath 102 to the delivery catheter.

In this manner, a plurality of differently configured intraluminal prostheses 228 can be stored in a compressed position, ready for use, and may be selectively attached to the delivery catheter as desired. For example, the intraluminal prosthesis 228 may be made of metal, plastic, or any other suitable material and may have a braided, coiled, woven, latticed, or any other suitable structure. Because the delivery catheters need not be connected to and stored with each intraluminal prosthesis cartridge 120 as in the prior art, a wide variety of intraluminal prosthesis choices can be presented to the surgeon without requiring excessive operating room space or a narrowed selection in advance of the surgery. Alternatively, the intraluminal prosthesis can be compressed shortly before use, possibly in the operating room or in a nearby laboratory or preparation room.

FIG. 2A depicts an exploded view of the intraluminal prosthesis cartridge 120 including a compressed intraluminal prosthesis 228. The intraluminal prosthesis 228 may be compressed for use with the apparatus 100 according to the present invention in any suitable manner. One method of compressing the intraluminal prosthesis 228 is described in greater detail in copending U.S. Sarac et al. Patent Application entitled "Method and Apparatus for Compressing Intraluminal Prostheses", Attorney Docket No. CCF-7587NP-2, which claims priority from U.S. Provisional Application No. 60/738,107, both of which are hereby incorporated by reference in their entirety.

As shown in FIG. 2B, the delivery catheter 230 has longitudinally spaced proximal and distal catheter ends 232 and 234, respectively, and is adapted to guide the intraluminal prosthesis cartridge 120 inside the patient's body. The delivery catheter 230 includes a catheter inner sheath 236 having longitudinally spaced proximal and distal catheter inner sheath ends 238 and 240, respectively, and a hollow catheter inner sheath bore 242. An outer sheath 244, when present, has longitudinally spaced proximal and distal outer sheath ends 246 and 248, respectively, and a hollow outer sheath bore 250 which at least partially surrounds the catheter inner sheath 236.

The inner sheath connector 126 may connect the cartridge inner sheath 102 and the catheter inner sheath 236 to form an inner sheath structure. Additionally, an outer-intraluminal prosthesis sheath connector 252 may connect the intraluminal prosthesis sheath 110 and the outer sheath 244 to form an outer sheath structure with the inner sheath structure contained within. The inner sheath connector 126 and outer-intraluminal prosthesis sheath connector 252, when present, assist in forming a unitary apparatus 100 from the separate delivery catheter 230 and intraluminal prosthesis cartridge 120. The inner sheath connector 126 or components thereof may be located on either or both of the proximal cartridge inner sheath end 102 and the distal catheter inner sheath end 236. Similarly, the outer-intraluminal prosthesis sheath connector 252, or components thereof, may be located on either or both of the proximal intraluminal prosthesis sheath end 110 and the distal outer sheath end 244. The inner sheath connector 126 and outer-intraluminal prosthesis sheath connector 252 may be of any suitable type and need not be of the same type for use with a single apparatus 100.

An example of a connector structure 354 suitable for use as an inner sheath connector 126 and/or an outer-intraluminal prosthesis sheath connector 252 is shown in FIG. 3. The depicted connector structure 354 is mounted on one of the two sheaths to be connected and engages the other of the two sheaths in an interference or frictional fit relationship. An adhesive may be used to enhance engagement of the connector structure 354 shown or of any other structure used as an inner sheath connector 126 and/or an outer-intraluminal prosthesis sheath connector 252. Examples (not shown) of other suitable connector structures include friction sleeves, heat-shrink tubing, cements or other adhesives, screw-thread couplers, spring-loaded couplers, captured-ball couplers, or any other structures chosen as desired by one of ordinary skill in the art. Additionally, the inner sheath connector 126 and/or outer-intraluminal prosthesis sheath connector 252 may have a tapered or variable cross-section to facilitate connection of two sheaths having different outside or inside diameters.

The delivery catheter 230 also includes a handle 256 attached to the proximal outer sheath end 246 and the proximal inner sheath end 238. The handle 256 is adapted to selectively control longitudinal movement of the intraluminal prosthesis sheath 110 between the first and second positions. More specifically, the handle 256 assists in moving the intraluminal prosthesis sheath 110 longitudinally with respect to the cartridge inner sheath 102 from the first position to the second position to release the compressed intraluminal prosthesis 228 from the annular intraluminal prosthesis space. Though the motion of the intraluminal prosthesis sheath 110 will be discussed hereafter as being "longitudinal", it should be understood that the motion of the intraluminal prosthesis sheath 110 could also or instead include at least some rotational, twisting, or other transverse component, whether or not intentionally. In other words, the motion of the intraluminal prosthesis sheath 110 is not necessarily purely one-dimensional, but that for the purposes of clarity, motion described as "longitudinal" herein optionally includes some amount of rotation.

The handle 256 may include at least one moveable part, such as a dial, lever, slider, or the depicted button 258 hereafter referenced, and optionally a plurality of detents 260, as shown in FIG. 2B, to move the intraluminal prosthesis sheath 110. The button 258 may be connected to the outer sheath 244 directly, for a directly proportional movement of the intraluminal prosthesis sheath 110 and the button. Alternately, some mechanical advantage device (not shown) may change the proportionality of movement between the intraluminal prosthesis sheath 110 and the button 258. The detents 260, when present, may be helpful in indicating how far the intraluminal prosthesis sheath 110 has been moved longitudinally, particularly when the movement of the button 258 is directly proportional with that of the intraluminal prosthesis sheath 110. Whether or not detents 260 are provided, a scale (not shown) could be marked on the handle 256 to help indicate the amount of movement of the intraluminal prosthesis sheath 110. A latch/safety structure (not shown) may be provided to help avoid accidental movement of the intraluminal prosthesis sheath 110 by requiring some affirmative action by the user before the intraluminal prosthesis sheath can be released for longitudinal motion. One of ordinary skill in the art can readily design a suitable handle 256, including a retraction system for the intraluminal prosthesis sheath 110, for a desired application of the present invention. The handle 256 may be designed for operation with one hand, so that the user can support the delivery catheter 230 or perform another task with the other hand while the intraluminal prosthesis 228 is being released from the annular intraluminal prosthesis space.

Figure 4:
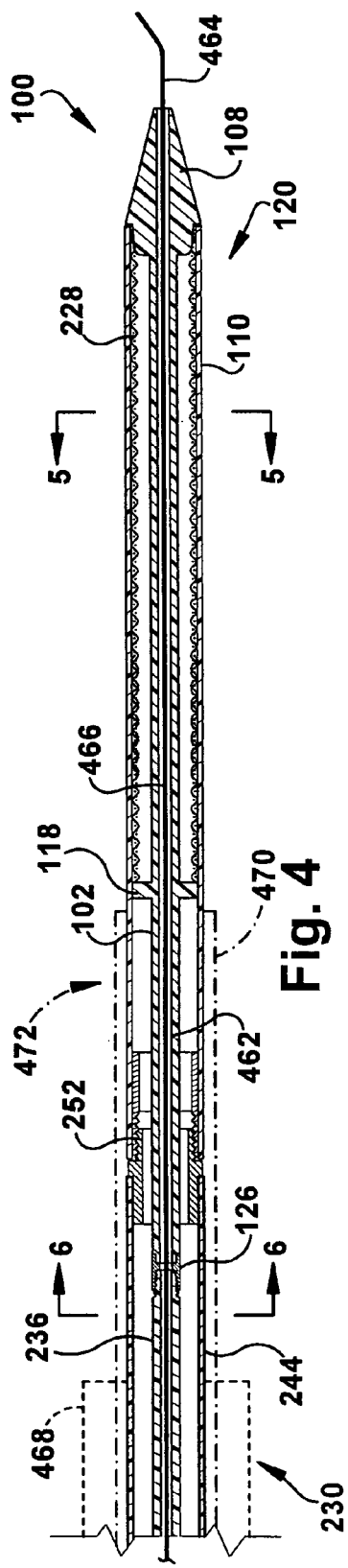
FIG. 4 is a partial cross-sectional view of the embodiment of FIGS. 2A and 2B.

FIG. 4 shows a cross-sectional view of the apparatus 100 of FIGS. 2A and 2B in an assembled state, with the delivery catheter 230 and intraluminal prosthesis cartridge 120 coupled together so that the cartridge inner sheath 102 and catheter inner sheath 236 extend co-linearly and the intraluminal prosthesis sheath 110 and outer sheath 244 extend co-linearly. In the assembly of FIG. 4, at least a portion of the inner sheath assembly has a hollow inner sheath bore 462 and the nose cone includes a hollow nose cone bore (not shown) extending co-linearly with the inner sheath bore. A guidewire 464 extends through the inner sheath bore 462 and the nose cone bore. The guidewire 464 may extend from (or through) the handle 256, through the catheter inner sheath bore 242 and a cartridge inner sheath bore 466 and to or through the nose cone 108, or the guidewire may enter the apparatus 100 through a side perforation (not shown) in any structure of the apparatus, as needed. The guidewire 464, when present, acts to help guide the apparatus 100 into and through the patient's body to a desired intraluminal prosthesis placement position in a known manner.

Optionally, an introducer tube 468 (e.g., a trocar), shown in dashed line in FIG. 4, may be used to introduce the apparatus 100, and thus the included intraluminal prosthesis 228, into the patient's body. When present, the introducer tube 468 is placed into the patient's body via a cut-down to a major blood vessel, other body lumen, or the like (not shown), and the apparatus 100 is inserted into the introducer tube 468, which encloses the apparatus to avoid unwanted contact with adjacent body structures of the patient. The introducer tube 468 acts to guide the apparatus 100 into the patient's body lumen in a known manner.

The introducer tube 468 is a short length of hollow material for easing the insertion of the apparatus 100 into the patient's body. The apparatus 100, however, may include a guard sheath 470, shown in dash-dot line in FIG. 4, which is a much longer structure and is adapted for insertion deep into the patient's body along with the delivery catheter 230 and intraluminal prosthesis cartridge 120. The guard sheath 470 has longitudinally spaced proximal and distal guard sheath ends and a hollow guard sheath bore. The distal guard sheath end 472 is located adjacent the intraluminal prosthesis cartridge 120. At least a portion of the intraluminal prosthesis sheath 110 is disposed within the hollow guard sheath bore when the intraluminal prosthesis sheath is in the second, open, position. Preferably, the intraluminal prosthesis sheath 110 is at least partially telescoped within the guard sheath 470, to avoid interference between the proximal intraluminal prosthesis sheath end 112 and the distal guard sheath end 472 during retraction of the intraluminal prosthesis sheath 110.

The guard sheath 470, when present, may serve to reduce friction on the intraluminal prosthesis sheath 110 during retraction and also may help avoid catching or snagging of the wall of the body lumen during movement by the leading-edge proximal intraluminal prosthesis sheath end 112.

It is contemplated that a balloon (not shown) could be provided to help expand the intraluminal prosthesis 228. A balloon may be especially useful if the intraluminal prosthesis is not self-expanding, but could be used with even a self-expanding intraluminal prosthesis if desired. One of ordinary skill in the art could readily provide the inflation lumen within the apparatus 100, as well as include the balloon within the compressed intraluminal prosthesis, for such an application of the present invention. When such a balloon is provided, it should be inserted into the intraluminal prosthesis (preferably before the intraluminal prosthesis is compressed) and then inflated in a known manner at the desired time to expand the compressed intraluminal prosthesis.

It is also contemplated that the apparatus 100 may be assembled in such a way that the inner sheath connector 126 and/or the outer-intraluminal prosthesis sheath connector 252 are not needed. The function of the two-connector system is mainly to allow just the intraluminal prosthesis cartridge 120 to be handled when crimping and sheathing the intraluminal prosthesis 228. In the embodiment of the Figures, it is deemed easier to crimp the intraluminal prosthesis 228 and then attach the intraluminal prosthesis cartridge 120 to the delivery catheter 230 than to crimp the intraluminal prosthesis while both the intraluminal prosthesis cartridge and delivery catheter are attached together as one lengthy system.

Figure 6:
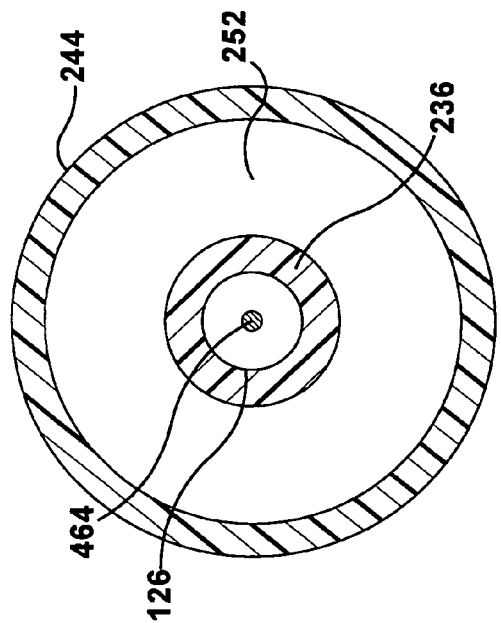
FIG. 6 is a cross-section taken along line 6-6 of FIG. 4.
Figure 5:
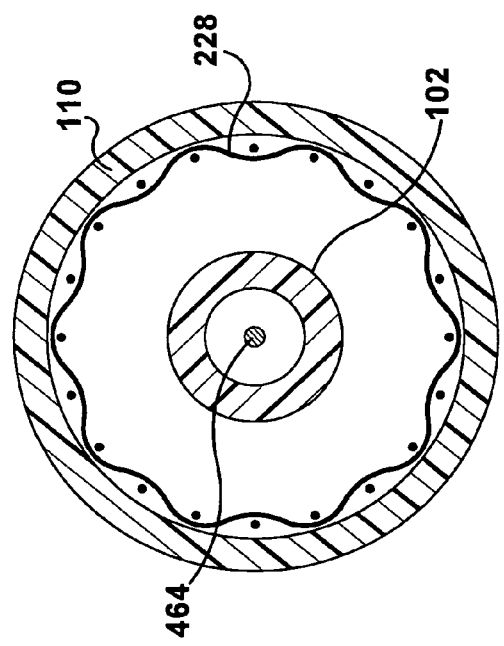
FIG. 5 is a cross-section taken along line 5-5 of FIG. 4.

FIG. 5 is a cross-sectional view of the intraluminal prosthesis cartridge 120, taken along line 5-5 of FIG. 4 and facing the proximal cartridge end 122. FIG. 6 is a cross-sectional view of the delivery catheter 230, taken along line 6-6 of FIG. 4 and facing the distal catheter end 234. The concentric arrangement of the structures of the intraluminal prosthesis cartridge 120 and delivery catheter 230 are shown in FIGS. 5 and 6, respectively. However, additional structures, such as the optional guidewire 464 shown, may be included in the embodiment of FIGS. 5 and 6. Also, certain structures of the present invention may be placed asymmetrically with respect to other structures, instead of in the regular, centered arrangement shown in FIGS. 5 and 6.

When the apparatus 100 is being prepared to deliver an intraluminal prosthesis 228 within the patient's body, the intraluminal prosthesis cartridge 120 and delivery catheter 230 should be chosen to optimize efficiency, accuracy, or any other desired quality. For example, the intraluminal prosthesis cartridge 120 may be chosen from among a plurality of different available intraluminal prosthesis cartridges 120 based upon at least one of an intraluminal prosthesis 228 dimension, an intraluminal prosthesis 228 material, an intraluminal prosthesis 228 configuration, an intraluminal prosthesis cartridge 120 dimension, or any other factor. Likewise, the delivery catheter 230 may be chosen from among a plurality of different available delivery catheters 230 based upon at least one of a delivery catheter 230 dimension, a delivery catheter 230 material, a delivery catheter 230 configuration, or any other factor.

Next, the chosen delivery catheter 230 is attached to the chosen intraluminal prosthesis cartridge 120 to create the apparatus 100. This can be accomplished by forming an inner sheath structure with the cartridge inner sheath 102 and the catheter inner sheath 236, optionally via an inner sheath connector 126, and by forming an outer-intraluminal prosthesis sheath structure with the intraluminal prosthesis sheath 110 and the outer sheath 244, optionally via an outer-intraluminal prosthesis sheath connector 252. Once the connections have been made, the apparatus 100 is ready for use.

The intraluminal prosthesis cartridge 120, with the contained compressed intraluminal prosthesis 228, is next inserted into the patient's body. This can be accomplished in any manner, such as by using a Seldinger or cut-down surgical technique. The delivery catheter 230 then may be used to guide the intraluminal prosthesis cartridge 120 to a desired intraluminal prosthesis 228 placement location within the patient's body.

Figure 7A:
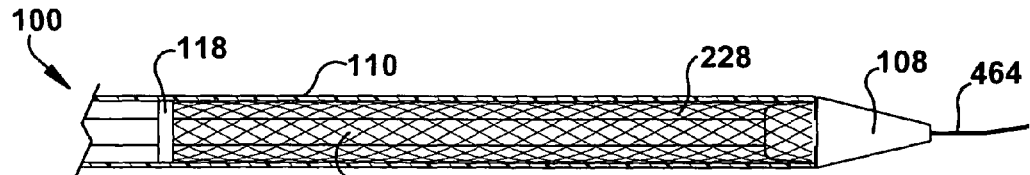
FIG. 7A is a partial side view of the embodiment of FIG. 3.

FIGS. 7A through 7E depict the sequence of operation of a portion of the apparatus 100 according to the present invention, once the intraluminal prosthesis cartridge 120 has reached the desired placement location. The intraluminal prosthesis 228 depicted in these Figures is presumed to be of the self-expanding type, but the apparatus 100 could be readily designed to instead or also deploy a balloon-expanded intraluminal prosthesis. FIG. 7a shows the apparatus 100 in the insertion configuration with the intraluminal prosthesis sheath 110 in the first position, having arrived at the desired placement location but before any steps have been taken to deploy the intraluminal prosthesis 228.

Figure 7B:
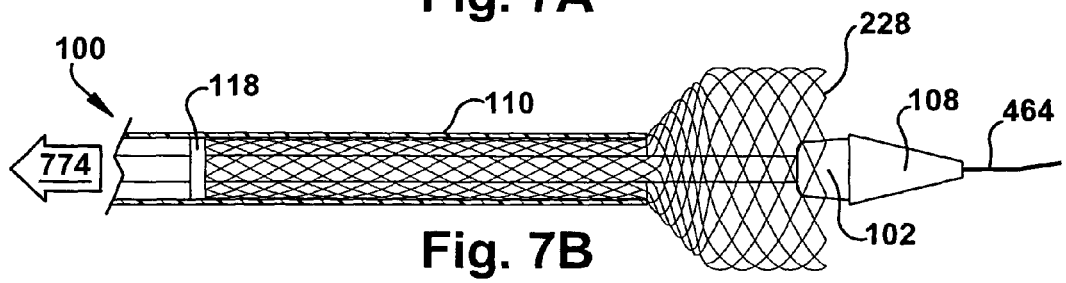
FIG. 7B is a partial side view of the embodiment of FIG. 3.

In FIG. 7B, the cartridge inner sheath 102 and the compressed intraluminal prosthesis 228 are being maintained at the desired placement location while the intraluminal prosthesis sheath 110 is starting to move longitudinally away from the desired placement location relative to the cartridge inner sheath 102 and the compressed intraluminal prosthesis 228 and toward the second position. The intraluminal prosthesis sheath 110 may be moved by actuation of a manual or automatic retraction system, such as the button 258 shown in FIG. 2B, in the handle 256. In the Figures, the intraluminal prosthesis sheath 110 moves longitudinally relative to the cartridge inner sheath 102 and the compressed intraluminal prosthesis 228 in a retraction direction 774. However, one of ordinary skill in the art could readily design an apparatus 100 in which the intraluminal prosthesis sheath 110 moves in a direction opposite the depicted retraction direction 774 to release the intraluminal prosthesis 228.

Figure 7C:
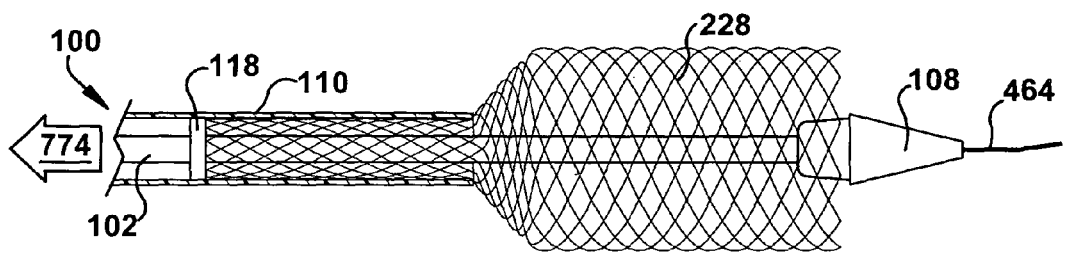
FIG. 7C is a partial side view of the embodiment of FIG. 3.

In FIG. 7C, the intraluminal prosthesis sheath 110 continues to move in the retraction direction 774 and the intraluminal prosthesis 228 is expanding at the desired placement location to form an expanded intraluminal prosthesis. Because the intraluminal prosthesis 228 of the Figures is self-expanding, the intraluminal prosthesis sheath 110 is merely releasing the self-expanding intraluminal prosthesis from confinement and allowing the self-expanding intraluminal prosthesis to expand. A self-expanding intraluminal prosthesis 228 should be chosen to have an inner diameter of sufficient size to allow the nose cone 108 to pass therethrough after the intraluminal prosthesis is released into a resting configuration at the desired placement location.

Though the stopper 118 is depicted in the Figures as being longitudinally separated from the intraluminal prosthesis 228 for clarity, the stopper 118 may instead be located immediately adjacent the intraluminal prosthesis in order to provide a "backstop" function. The intraluminal prosthesis sheath 110 may tend to exert a frictional drag force on the intraluminal prosthesis 228, particularly a self-expanding intraluminal prosthesis, as the intraluminal prosthesis sheath moves in the retraction direction 774. A "backstop"-positioned stopper 118 counters that drag force to maintain the intraluminal prosthesis 228 at or near the desired placement location while the intraluminal prosthesis sheath 110 moves relatively thereto.

Figure 7D:
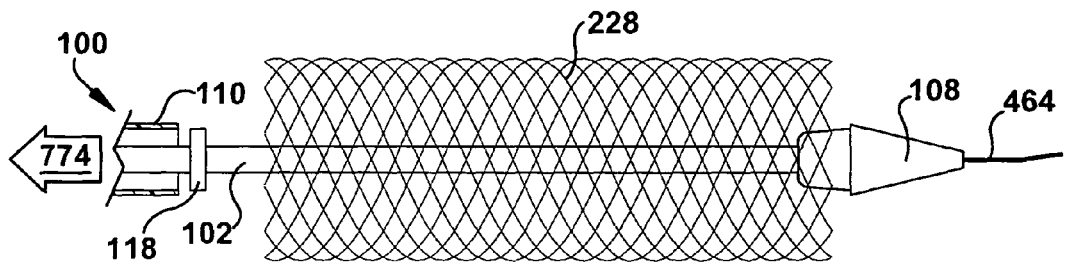
FIG. 7D is a partial side view of the embodiment of FIG. 3.
Figure 7E:
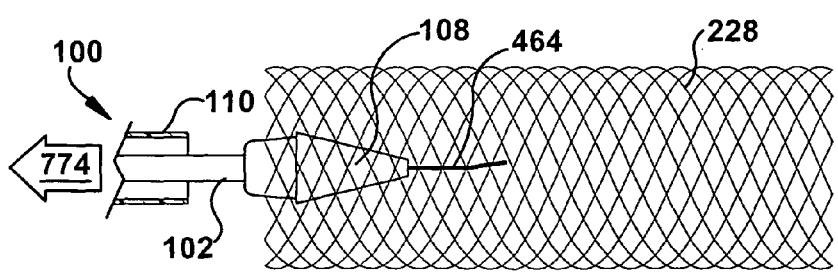
FIG. 7E is a partial side view of the embodiment of FIG. 3.

In FIG. 7D, the intraluminal prosthesis 228 is fully deployed from the intraluminal prosthesis cartridge 120 and the intraluminal prosthesis sheath 110 is in the second position. The apparatus 100 may now be removed from the patient's body, as shown in FIG. 7E. This removal may be accomplished simply by manipulating the delivery catheter 230 to pull the cartridge inner sheath 102 and attached nose cone 108 back toward the direction from which they initially approached the desired placement location (the retraction direction 774, in the orientation of FIGS. 7A-7E). The now-expanded intraluminal prosthesis 228 remains at the desired placement location. The guidewire 464 may be removed along with the rest of the apparatus 100 or optionally remains in place for further surgical procedures as desired. For instance, a balloon catheter (not shown) or similar apparatus could be inserted into the expanded intraluminal prosthesis 228 after the intraluminal prosthesis cartridge 120 has been removed from the desired placement location to further expand the intraluminal prosthesis.

While aspects of the present invention have been particularly shown and described with reference to the preferred embodiment above, it will be understood by those of ordinary skill in the art that various additional embodiments may be contemplated without departing from the spirit and scope of the present invention. For example, the sheaths or any other components of the present invention may be made from PTFE, PEEK, Polyimide, nitinol, or other suitable material or combination of materials. The intraluminal prosthesis sheath 110 could be pulled by a wire to telescopically retract into the outer sheath 244. A rotation wheel or variable slider could be provided on the handle 256 to retract the intraluminal prosthesis sheath 110. A lubricant, in either a flowing or coating form, may be provided to the structures of the apparatus 100 which move relative to other structures. When the intraluminal prosthesis 228 has temperature-responsive properties, a suitable catheter could be inserted into the intraluminal prosthesis before or after expansion to actuate those temperature-responsive properties. The intraluminal prosthesis 228 may be lined, with a layer of synthetic or biological material covering at least part of an inner or outer surface of the intraluminal prosthesis. Any of the structures of the apparatus 100 may be relatively moved or repositioned, temporarily or permanently, as desirable to facilitate assembly or use of the apparatus. A device or method incorporating any of these features should be understood to fall under the scope of the present invention as determined based upon the claims below and any equivalents thereof.

The method and apparatus of certain embodiments of the present invention, when compared with other apparatus and methods, may have the advantages of avoiding damage to the intraluminal prosthesis, allowing surgeons to select an intraluminal prosthesis without regard to compressed size, and providing a modular system for efficiency and economy in storage and selection. Such advantages are particularly worthy of incorporating into the design, manufacture, and operation of intraluminal prosthesis delivery apparatus. In addition, the present invention may provide other advantages which have not yet been discovered.

Other aspects, objects, and advantages of the present invention can be obtained from a study of the drawings, the disclosure, and the appended claims.

Having described the invention, the following is claimed:

1. An apparatus for delivering an intraluminal prosthesis within a patient's body, the apparatus comprising:
   an inner sheath having longitudinally spaced proximal and distal inner sheath ends;
   a nose cone connected to the distal inner sheath end;
   an intraluminal prosthesis sheath having longitudinally spaced proximal and distal intraluminal prosthesis sheath ends and a hollow intraluminal prosthesis sheath bore at least partially surrounding the inner sheath, the intraluminal prosthesis sheath being adapted for movement relative to the inner sheath;

a stopper connected to the inner sheath at a location longitudinally spaced from the nose cone and extending radially between the inner sheath and the intraluminal prosthesis sheath; and an annular intraluminal prosthesis space defined radially between the intraluminal prosthesis sheath and the inner sheath and longitudinally between the stopper and the nose cone, the annular intraluminal prosthesis space being adapted to contain a compressed intraluminal prosthesis;

wherein the inner sheath, the nose cone, the stopper, the intraluminal prosthesis sheath, and the annular intraluminal prosthesis space cooperatively form an intraluminal prosthesis cartridge having proximal and distal cartridge ends spaced apart by a cartridge body located longitudinally therebetween, the cartridge body including the annular intraluminal prosthesis space, the proximal cartridge end including the proximal inner sheath end, the proximal cartridge end being configured for mechanical attachment to a distal end of a delivery catheter, the intraluminal prosthesis cartridge being separate from the delivery catheter until attached thereto;

wherein the proximal inner sheath end has an inner sheath connector configured to attach to a distal inner sheath end of the delivery catheter, the proximal intraluminal prosthesis sheath end has an outer-intraluminal prosthesis sheath connector configured to attach to a distal outer sheath end of the delivery catheter, and the inner sheath connector and outer-intraluminal prosthesis sheath connector are both inserted into the patient's body for delivery of the intraluminal prosthesis.

2. The apparatus of claim 1, wherein the inner sheath includes a hollow inner sheath bore and the nose cone includes a hollow nose cone bore extending co-linearly with the inner sheath bore, the inner sheath bore and the nose cone bore being adapted to accept a guidewire extending therethrough.

3. The apparatus of claim 1, wherein the proximal inner sheath end includes an inner sheath connector adapted to connect the inner sheath to the distal end of the delivery catheter.

4. The apparatus of claim 1, wherein the proximal intraluminal prosthesis sheath end includes an outer-intraluminal prosthesis sheath connector adapted to connect the intraluminal prosthesis sheath to the distal end of the delivery catheter.

5. The apparatus of claim 1, wherein the intraluminal prosthesis sheath is adapted for at least one of longitudinal and rotational movement relative to the inner sheath.

6. The apparatus of claim 1, wherein the intraluminal prosthesis sheath moves at least one of longitudinally and rotationally with respect to the inner sheath to release the compressed intraluminal prosthesis from the annular intraluminal prosthesis space.

7. The apparatus of claim 6, wherein the intraluminal prosthesis sheath is actuated for at least one of longitudinal and rotational movement by the delivery catheter.

8. The apparatus of claim 1, wherein the intraluminal prosthesis cartridge is at least partially enclosed within an introducer tube for placement into the patient's body.

9. The apparatus of claim 1, wherein the compressed intraluminal prosthesis occupies a majority of the longitudinal dimension of the cartridge body when located within the annular intraluminal prosthesis space.

10. An intraluminal prosthesis delivery apparatus, comprising:

an intraluminal prosthesis cartridge having longitudinally spaced proximal and distal cartridge ends and adapted to contain a compressed intraluminal prosthesis; and a delivery catheter having longitudinally spaced proximal and distal catheter ends and adapted to guide the intraluminal prosthesis cartridge inside the patient's body while the distal catheter end is located within the patient's body;

the distal catheter end and proximal cartridge end being configured for mechanical attachment to one another to form the apparatus, the intraluminal prosthesis cartridge being separate from the delivery catheter until the apparatus is formed, wherein the intraluminal prosthesis cartridge includes:

an inner sheath having longitudinally spaced proximal and distal inner sheath ends and a hollow inner sheath bore;

a nose cone located at the cartridge distal end and connected to the distal inner sheath end;

an intraluminal prosthesis sheath having longitudinally spaced proximal and distal intraluminal prosthesis sheath ends and a hollow intraluminal prosthesis sheath bore at least partially surrounding the inner sheath, the intraluminal prosthesis sheath being adapted for at least one of longitudinal and rotational movement relative to the inner sheath between a first position and a second position;

a stopper connected to the inner sheath at a location longitudinally spaced from the nose cone and extending radially between the inner sheath and the intraluminal prosthesis sheath; and an annular intraluminal prosthesis space defined radially between the intraluminal prosthesis sheath in the first position and the inner sheath and longitudinally between the stopper and the nose cone, the annular intraluminal prosthesis space being adapted to contain a compressed intraluminal prosthesis;

wherein the intraluminal prosthesis cartridge has proximal and distal cartridge ends spaced apart by a cartridge body located longitudinally therebetween, the cartridge body including the annular intraluminal prosthesis space, the proximal cartridge end including the proximal inner sheath end, the proximal cartridge end being configured for mechanical attachment to the distal end of the delivery catheter;

wherein the proximal inner sheath end has an inner sheath connector configured to attach to a distal inner sheath end of the delivery catheter, the proximal intraluminal prosthesis sheath end has an outer-intraluminal prosthesis sheath connector configured to attach to a distal outer sheath end of the delivery catheter, and the inner sheath connector and outer-intraluminal prosthesis sheath connector are both inserted into the patient's body for delivery of the intraluminal prosthesis.

11. The intraluminal prosthesis delivery apparatus of claim 10, wherein the inner sheath is a cartridge inner sheath having a hollow cartridge inner sheath bore, and the delivery catheter includes: a catheter inner sheath having longitudinally spaced proximal and distal catheter inner sheath ends and a hollow catheter inner sheath bore; an outer sheath having longitudinally spaced proximal and distal outer sheath ends and a hollow outer sheath bore at least partially surrounding the catheter inner sheath; and a handle attached to the proximal outer sheath end and the proximal catheter inner sheath end, the handle being adapted to selectively control at least one of longitudinal and rotational movement of the intraluminal prosthesis sheath between the first and second positions.

12. The intraluminal prosthesis delivery apparatus of claim 11, including an inner sheath connector connecting the cartridge inner sheath and the catheter inner sheath.

13. The intraluminal prosthesis delivery apparatus of claim 12, wherein the inner sheath connector connects the cartridge inner sheath and the catheter inner sheath such that the cartridge inner sheath bore is co-linear with the catheter inner sheath bore, and a guidewire extends through the cartridge inner sheath bore and the catheter inner sheath bore.

14. The intraluminal prosthesis delivery apparatus of claim 13, wherein the nose cone includes a hollow nose cone bore extending co-linearly with respect to the cartridge inner sheath bore and the guidewire extends through the nose cone bore.

15. The intraluminal prosthesis delivery apparatus of claim 11, including an outer-intraluminal prosthesis sheath connector connecting the intraluminal prosthesis sheath and the outer sheath.

16. The intraluminal prosthesis delivery apparatus of claim 11, wherein the handle moves the intraluminal prosthesis sheath longitudinally with respect to the cartridge inner sheath from the first position to the second position to release the compressed intraluminal prosthesis from the annular intraluminal prosthesis space.

17. The intraluminal prosthesis delivery apparatus of claim 11, including a guard sheath having longitudinally spaced proximal and distal guard sheath ends and a hollow guard sheath bore, the distal guard sheath end being adjacent the intraluminal prosthesis cartridge and at least a portion of the intraluminal prosthesis sheath being disposed within the hollow guard sheath bore when the intraluminal prosthesis sheath is in the second position.

18. The intraluminal prosthesis delivery apparatus of claim 10, wherein an introducer tube at least partially encloses the apparatus for placement into a patient's body.

19. The intraluminal prosthesis delivery apparatus of claim 10, wherein the intraluminal prosthesis cartridge is chosen from among a plurality of different intraluminal prosthesis cartridges based upon at least one of an intraluminal prosthesis dimension, an intraluminal prosthesis material, an intraluminal prosthesis configuration, and a cartridge dimension.

20. The intraluminal prosthesis delivery apparatus of claim 10, wherein the compressed intraluminal prosthesis occupies a majority of the longitudinal dimension of the cartridge body when located within the annular intraluminal prosthesis space.

* * * * *